US010774032B2

(12) United States Patent
Gao et al.

(10) Patent No.: US 10,774,032 B2
(45) Date of Patent: Sep. 15, 2020

(54) ORGANOMETAL HALIDE PEROVSKIT NANOPLATELETS, DEVICES, AND METHODS

(71) Applicant: Florida State University Research Foundation, Inc., Tallahassee, FL (US)

(72) Inventors: Hanwei Gao, Tallahassee, FL (US); Biwu Ma, Tallahassee, FL (US); Yichuan Ling, Tallahassee, FL (US); Zhao Yuan, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 512 days.

(21) Appl. No.: 15/272,572

(22) Filed: Sep. 22, 2016

(65) Prior Publication Data
US 2017/0084848 A1    Mar. 23, 2017

Related U.S. Application Data
(60) Provisional application No. 62/221,973, filed on Sep. 22, 2015.

(51) Int. Cl.
| | |
|---|---|
| *H01L 51/54* | (2006.01) |
| *C09K 11/06* | (2006.01) |
| *C07C 209/68* | (2006.01) |
| *C09K 11/02* | (2006.01) |
| *C07C 211/63* | (2006.01) |
| *H05B 33/14* | (2006.01) |
| *C09K 11/66* | (2006.01) |
| *H01L 51/42* | (2006.01) |
| *H01L 51/00* | (2006.01) |
| *H01L 51/50* | (2006.01) |
| *B82Y 40/00* | (2011.01) |
| *B82Y 20/00* | (2011.01) |

(52) U.S. Cl.
CPC .......... *C07C 209/68* (2013.01); *C07C 211/63* (2013.01); *C09K 11/025* (2013.01); *C09K 11/06* (2013.01); *C09K 11/664* (2013.01); *H01L 51/4246* (2013.01); *H05B 33/14* (2013.01); *B82Y 20/00* (2013.01); *B82Y 40/00* (2013.01); *C09K 2211/10* (2013.01); *C09K 2211/188* (2013.01); *H01L 51/007* (2013.01); *H01L 51/0037* (2013.01); *H01L 51/0042* (2013.01); *H01L 51/5012* (2013.01); *H01L 2251/308* (2013.01); *Y02E 10/549* (2013.01); *Y02P 70/521* (2015.11); *Y10S 977/755* (2013.01); *Y10S 977/896* (2013.01); *Y10S 977/95* (2013.01)

(58) Field of Classification Search
CPC ............... Y02E 10/549; Y10S 977/755; Y10S 977/896; Y10S 977/95; Y02P 70/521; H05B 33/14; H05B 33/20; B82Y 20/00; B82Y 40/00; C09K 11/025; C09K 11/06; C09K 11/664; C09K 2211/00; C09K 2211/10; C09K 2211/188; C07C 209/68; C07C 211/63; H01L 51/0032; H01L 51/0037; H01L 51/0042; H01L 51/007; H01L 51/50; H01L 51/5012; H01L 51/502; H01L 51/4246; H01L 2251/308
See application file for complete search history.

(56) References Cited

U.S. PATENT DOCUMENTS

| | | | |
|---|---|---|---|
| 6,420,056 B1 * | 7/2002 | Chondroudis et al. | ...................... B82Y 10/00 313/502 |
| 2005/0006625 A1 * | 1/2005 | Seo et al. .............. | C07D 213/74 252/301.16 |
| 2005/0126628 A1 * | 6/2005 | Scher et al. ........... | B82Y 10/00 136/263 |
| 2010/0294355 A1 * | 11/2010 | Choi et al. ........ | H01L 31/03528 136/256 |

OTHER PUBLICATIONS

Jang et al., "Reversible Halide Exchange Reaction of Organometal Trihalide Perovskite Colloidal Nanocrystals for Full-Range Band Gap Tuning", Nano. Lett. 2015, 15, pp. 5191-5199 (published Jul. 10, 2015) and supporting information pp. S1-S22.*

Supporting information for "Shape Evolution and Single Particle Luminescence of Organometal Perovskite Nanocrystals", Zhu et al., ACSNano (2015), 14 pages.*

PCT International Search Report and Written Opinion for PCT Application No. PCT/US2016/053013 dated Dec. 7, 2016 (11 pages).

Agyuler et al., "Light-Emitting Electrochemical Cells Based on Hybrid Lead Halide Perovskite Nanoparticles," J. Phys. Chem. C, 2015, 119:12047-12054.

Zhu et al., "Shape Evolution and Single Particle Luminescence of Organometal Halide Perovskite Nanocrystals," ACS Nano, 2015, 9(3):2948-2959.

Jang et al., "Reversible Halide Exchange Reaction of Organometal Trihalide Perovskite Colloidal Nanocrystals for Full-Range Band Gap Tuning," Nano Lett., 2015, 15:5191-5199.

Noel et al., "Enhanced Photoluminescence and Solar Cell Performance via Lewis Base Passivation of Organic-Inorganic Lead Halide Perovskites," ACS Nano, 2014, vol. 8, 21 pages.

Schmidt et al., "Nontemplate Synthesis of CH3NH3PbBr3 Perovskite Nanoparticles," J. Am. Chem. Soc., 2014, 136:850-853.

Tyagi et al., "Colloidal Organohalide Perovskite Nanoplatelets Exhibiting Quantum Confinement," J. Phys. Chem. Lett., 2015, 6(10):1911-1916.

(Continued)

*Primary Examiner* — Andrew K Bohaty
(74) *Attorney, Agent, or Firm* — Eversheds Sutherland (US) LLP

(57) ABSTRACT

Provided herein are metal halide perovskite nanoplatelets, methods for making metal halide perovskite nanoplatelets, and devices and composite materials that include metal halide nanoperovskite nanoplatelets. The metal halide perovskite nanoplatelets may be stable at ambient temperature and pressure, thereby easing device fabrication.

22 Claims, 4 Drawing Sheets

(56) References Cited

OTHER PUBLICATIONS

Zhang et al., "Brightly Luminescent and Color-Tunable Colloidal CH3NH3PbX3 (X=Br, I, Cl) Quantum Dots: Potential Alternatives for Display Technology," ACS Nano, 2015, 9:4533-4542.

* cited by examiner

ORGANOMETAL HALIDE PEROVSKIT NANOPLATELETS, DEVICES, AND METHODS

CROSS-REFERENCE TO RELATED APPLICATIONS

This application claims priority to U.S. Provisional Patent Application No. 62/221,973, filed Sep. 22, 2015, which is incorporated herein by reference.

BACKGROUND

Solution-processable electronic materials have attracted attention, because they may have the potential to permit the low-cost, scalable fabrication of lightweight, flexible devices (see, e.g., Friend, R. H. et al. *Nature* 1999, 397, 121; and Shirasaki, Y. et al. *Nat. Photon.* 2013, 7, 13). Recently, earth-abundant organometal halide perovskites that can be solution processed have emerged as a new class of semiconductors for photovoltaic devices. They have the potential to offer one or more advantages, such as low temperature processing, tunable optical band gap, and favorable charge transport. These solution-processed perovskites have also shown promise in light emitting diodes (LEDs).

However, the performance of perovskite-based LEDs (PeLEDs) reported to date has not reached the level of performance typically associated with organic or quantum dot based LEDs that share similar device architecture and operating mechanisms (see, e.g., Shirasaki, Y. et al. *Nat. Photon.* 2013, 7, 13; and Yang, Y. et al. *Nat. Photon.* 2015, 9, 259). Effort has been made to optimize the device configurations and thin film morphology to improve the brightness and the quantum efficiency of PeLEDs. For example, interfacial engineering has been investigated to reduce the electron or hole injection barriers for efficient electroluminescence (EL) (Yu, J. C. et al. *Adv. Mater.* 2015, 27, 3492). Other devices that have been fabricated include an ionic conductive poly(ethylene oxide) that was used to form uniform perovskite/polymer composite thin films as emitting layers (Li, J. et al. *Adv. Mater.* 2015, 27, 5196).

It has been observed that the film quality and/or optical properties of bulk perovskite films can depend heavily on the choice of substrate (Wang, J. et al. *Adv. Mate.* 2015, 27, 2311).

Provided that bulk perovskite thin films often suffer from poor morphology and/or low luminescent quantum yield, researchers have attempted embedding highly luminescent perovskite nanocrystals in a pinhole-free matrix of dielectric polymer to generate better LED performance (Li G. et al. *Nano Lett.* 2015, 15, 2640).

Although luminescent colloid organometal halide perovskite nanoparticles with high quantum yields have been reported, no efficient PeLEDs that include perovskite nanoparticles have been demonstrated (see, e.g., Zhang, F. et al. *ACS Nano* 2015, 9, 4533; Jang, D. M. et al. *Nano Lett.* 2015, 15, 5191; Tyagi, P. et al. *J. Phys. Chem. Lett.* 2015, 6, 1911; Schmidt, L. C. et al. *J. Am. Chem. Soc.* 2014, 136, 850; and Noel, N. K. et al. *ACS Nano* 2014, 8, 9815).

Therefore, there remains a need for nanoscale perovskites and PeLEDs that include nanoscale perovskite materials that offer one or more of the following advantages: efficiency, bright luminescence, high charge carrier mobility, broadband color tunability, color purity with narrow-band emission, and/or morphological and/or optoelectronic properties that are not substantially influenced by the surface properties of substrates. Facile methods for producing nanoscale perovskite materials also are desired, including methods that do not require the preparation of amine halide salts and/or the use of inert conditions when fabricating devices or handling the nanoscale perovskites.

BRIEF SUMMARY

Provided herein are metal halide perovskite nanoplatelets. In embodiments, the nanoplatelets comprise an alkylammonium metal halide and a capping ligand. Each nanoplatelet may have a width of about 50 nm to about 300 nm and a length of about 50 nm to about 300 nm.

Also provided herein are composite materials comprising the metal halide perovskite nanoplatelets. In embodiments, the composite materials comprise at least one metal halide perovskite nanoplatelet, and a matrix material. The at least one metal halide perovskite nanoplatelet may be disposed in the matrix material.

Optoelectronic devices comprising the metal halide perovskite nanoplatelets and/or the composite materials comprising the metal halide perovskite nanoplatelets also are provided. In embodiments, the optoelectronic devices comprise a composite material that includes at least one metal halide perovskite nanoplatelet. The metal halide perovskite nanoplatelet may be a light emitting material. The optoelectronic devices may also include a substrate, an electrode disposed on the substrate, and a counter electrode. One or more metal halide perovskite nanoplatelets and/or a composite material that includes at least one metal halide perovskite nanoplatelet may be arranged between the electrode and the counter electrode.

Also provided herein are methods of forming a metal halide perovskite nanoplatelet. In embodiments, the methods comprise providing a precursor solution comprising a metal halide, a capping ligand, an alkylamine, a hydrogen halide acid of the formula HX, wherein X is a halogen, and at least one solvent; and contacting the precursor solution with a precipitating agent to precipitate the metal halide perovskite nanoplatelet.

DETAILED DESCRIPTION

Figure 1:
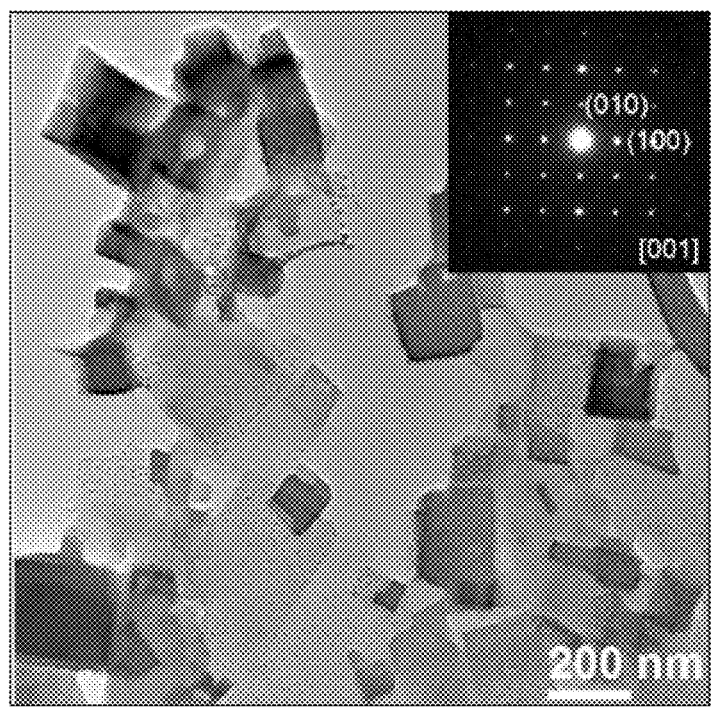
FIG. 1 is a transmission electron microscopy (TEM) image and a selected area electron diffraction (SAED) pattern (inset) of one embodiment of a metal halide perovskite nanoplatelet.

Provided herein are metal halide perovskite nanoplatelets that may have a bright, stable, and spectrally narrow emission, and/or be produced by a facile synthetic method that can be performed in an ambient environment. Moreover, embodiments of the methods of producing the metal halide perovskite nanoplatelets do not require the preparation of amine halide salts, and/or the use of extra organic solvents, such as oleic acid and 1-octadecene. And, in some embodiments, the metal halide perovskite nanoplatelets provided herein can have higher PL quantum yields than polycrystalline bulk perovskites.

Also provided herein are optoelectronic devices that include one or more of the metal halide perovskite nanoplatelets as a light emitting material. In embodiments, the morphological and optoelectronic properties of the metal halide perovskite nanoplatelet emitters are not substantially influenced by the surface properties of the underlying substrates. Therefore, the properties of the metal halide perovskite nanoplatelets provided herein can expand the [1] number of possible substrates and substrate materials, and/or [2] device configurations.

Moreover, the metal halide perovskite nanoplatelets, in embodiments, are stable in ambient conditions and/or moisture resistant. Therefore, optoelectronic devices that include the metal halide perovskite nanoplatelets may be produced in an ambient environment via a glovebox-free device fabrication. Unlike previous materials, the stability of certain embodiments of the metal halide perovskite nanoplatelets provided herein can allow for the preparation of light emitting materials to be independent from device fabrication. Therefore, more cost-effective deposition methods can be used to deposit the metal halide perovskite nanoplatelets disclosed herein.

Metal Halide Perovskite Nanoplatelets

Provided herein are metal halide perovskite nanoplatelets. The metal halide perovskite nanoplatelets, in embodiments, comprise an alkylammonium metal halide and a capping ligand.

The terms "nanoplatelet" and "nanoplatelets," as used herein, refer to a material having a surface, wherein at least one of the width and the length of the surface is at least 5 times greater than the average thickness of the material. For example, a nanoplatelet may have an average thickness of about 10 nm, and a surface having a length or width of at least 50 nm. If the nanoplatelet is substantially shaped like a square, rectangle, or parallelogram, then the length and width will correspond to the commonly understood lengths and widths of a square, rectangle, and parallelogram, respectively. If the nanoplatelet includes one or more angled sides, e.g., it is substantially trapezoidal in shape, then the length may correspond to the largest base, and the width may be measured at a right angle from the base and correspond to the largest dimension across the surface.

In embodiments, the nanoplatelets provided herein have a surface having a width of about 50 nm to about 300 nm and/or a length of about 50 nm to about 300 nm. In further embodiments, the nanoplatelets provided herein have a surface having a width of about 100 nm to about 300 nm and/or a length of about 100 nm to about 300 nm. In other embodiments, the nanoplatelets provided herein have a surface having a width of about 50 nm to about 250 nm and/or a length of about 50 nm to about 250 nm. The dimensions of the nanoplatelets may be determined by Transmission Electron Microscopy (TEM) images.

In embodiments, the alkylammonium metal halide of the metal halide perovskite nanoplatelets provided herein may include a $C_1$-$C_5$ alkylammonium metal halide. The $C_1$-$C_5$ alkylammonium moiety may include a straight or branched alkyl group, such as methyl, ethyl, propyl, butyl, isopropyl, t-butyl, pentyl, t-pentyl, isopentyl, sec-pentyl, neopentyl, etc. The metal may be selected from Sn, Cu, Ge, Mn, Co, Pb, Bi, or Eu. The halide may be chloride, bromide, or iodide. The alkylammonium metal halide may be an alkylammonium lead halide, alkylammonium tin halide, alkylammonium germanium halide, alkylammonium manganese halide, alkylammonium cobalt halide, alkylammonium bismuth halide, or alkylammonium europium halide. In one embodiment, the alkylammonium metal halide is a methylammonium metal halide. In another embodiment, the alkylammonium metal halide is a methylammonium lead halide, methylammonium tin halide, methylammonium germanium halide, methylammonium manganese halide, methylammonium cobalt halide, methylammonium bismuth halide, or methylammonium europium halide. In a further embodiment, the alkylammonium metal halide is a methylammonium lead bromide.

Generally, the capping ligand may be any ligand that is capable of forming a nanoplatelet with the alkylammonium metal halide. The capping ligand may be a compound according to the following formula:

wherein $R_1$ is a $C_1$-$C_{20}$ hydrocarbyl, and X is Cl, Br, or I. In one embodiment, $R_1$ is a monovalent $C_6$-$C_{20}$ hydrocarbyl. In a further embodiment, $R_1$ is a monovalent $C_8$-$C_{20}$ hydrocarbyl.

In embodiments, the capping ligand comprises a compound of the following formula:

wherein $R_1$ is a monovalent $C_1$-$C_{20}$ hydrocarbyl. In one embodiment, $R_1$ is a monovalent $C_6$-$C_{20}$ hydrocarbyl. In a further embodiment, $R_1$ is a monovalent $C_8$-$C_{20}$ hydrocarbyl. In a particular embodiment, $R_1$ is an unsubstituted, monovalent $C_8$ hydrocarbyl, and the capping ligand is octylammonium bromide.

The phrase "$C_1$-$C_{20}$ hydrocarbyl," as used herein, generally refers to aliphatic groups containing from 1 to 20 carbon atoms. Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having from 1 to about 20 carbon atoms. Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "substituted," when used to describe a chemical structure or moiety, refers to a derivative of that structure or moiety wherein one or more of its hydrogen atoms is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), tertiary amine (such as alkylamino, arylamino, arylalkylamino), aryl, aryloxy, azo, carbamoyl (—NHC(O)O-alkyl- or —OC(O)NH-alkyl), carbamyl (e.g., $CONH_2$, as well as CONH-alkyl, CONH-aryl, and CONH-arylalkyl), carboxyl, carboxylic acid, cyano, ester, ether (e.g., methoxy, ethoxy), halo, haloalkyl (e.g., —$CCl_3$, —$CF_3$, —$C(CF_3)_3$), heteroalkyl, isocyanate, isothiocyanate, nitrile, nitro, phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

The metal halide perovskite nanoplatelets provided herein may exhibit one or more unexpected properties. In one embodiment, the metal halide perovskite nanoplatelets have a quantum yield of about 65 to about 85% when disposed in toluene.

In embodiments, the metal halide perovskite nanoplatelets are stable, including in air with humidity of about 55% for at least one week. Unlike most bulk polycrystalline organometal perovskites, which must be prepared in a nitrogen glovebox due to their sensitivity to moisture, the metal halide perovskite nanoplatelets provided herein, in particular embodiments, can be stored in an ambient environment for at least a week, and, if desired, re-dispersed into an organic solvent for further use. The luminescent properties of the metal halide perovskite nanoplatelets provided herein can be substantially maintained during storage in an ambient environment for at least a week.

Methods of Forming Metal Halide Perovskite Nanoplatelets

In embodiments, the metal halide perovskite nanoplatelets may be synthesized with a modified ligand-assisted precipitation method.

In embodiments, the metal halide perovskite nanoplatelets are formed by a method comprising providing a precursor solution comprising a metal halide, a capping ligand, an alkylamine, a hydrogen halide acid of the formula HX, and at least one solvent; and contacting the precursor solution with a precipitating agent to precipitate the metal halide perovskite nanoplatelet, wherein X is a halogen. In one embodiment, the methods further comprise separating the metal halide perovskite nanoplatelet from substantially all of the at least one solvent and the precipitating agent. The metal halide perovskite nanoplatelet then may be dried.

The metal halide may be a compound according to the following formula:

wherein M is selected from Sn, Cu, Ge, Mn, Co, Pb, Bi, or Eu; X is Cl, Br, or I; and a is 2 or 3. In one embodiment, the metal halide is $PbBr_2$.

The capping ligand may be a compound according to the following formula:

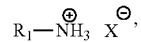

wherein $R_1$ is a $C_1$-$C_{20}$ hydrocarbyl, and X is Cl, Br, or I. In one embodiment, $R_1$ is a monovalent $C_6$-$C_{20}$ hydrocarbyl. In a further embodiment, $R_1$ is a monovalent $C_8$-$C_{20}$ hydrocarbyl.

In embodiments, the capping ligand comprises a compound of the following formula:

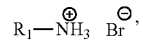

wherein $R_1$ is a monovalent $C_1$-$C_{20}$ hydrocarbyl. In one embodiment, $R_1$ is a monovalent $C_6$-$C_{20}$ hydrocarbyl. In a further embodiment, $R_1$ is a monovalent $C_8$-$C_{20}$ hydrocarbyl. In a particular embodiment, $R_1$ is an unsubstituted, monovalent $C_8$ hydrocarbyl, and the capping ligand is octylammonium bromide.

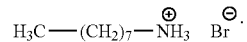

Not wishing to be bound by any particular theory, it was believed that the capping ligand may facilitate, at least in part, the formation of the nanoplatelets.

In embodiments, the metal halide is $PbBr_2$ and the capping ligand is octylammonium bromide.

The alkylamine may include a straight or branched alkyl moiety having from 1-20 carbon atoms, and a primary amine. In embodiments, the alkylamine is a $C_1$-$C_5$ alkyl amine. The $C_1$-$C_5$ alkylamine may include a straight or branched $C_1$-$C_5$ alkyl group, such as methyl, ethyl, propyl, butyl, isopropyl, t-butyl, pentyl, t-pentyl, isopentyl, sec-pentyl, neopentyl, etc., and a primary amine. In one embodiment, the alkylamine is methylamine.

In embodiments, the metal halide is $PbBr_2$, the capping ligand is octylammonium bromide, and the alkyl amine is methylamine.

The acid of the formula HX, in embodiments, can include HCl, HBr, HI, or a combination thereof. In one embodiment, the acid of the formula HX is HBr.

In embodiments, the metal halide is $PbBr_2$, the capping ligand is octylammonium bromide, the alkyl amine is methylamine, and the acid of the formula HX is HBr.

The precursor solution may be prepared by adding to a solvent, in any order or sequence, the metal halide, the capping ligand, the alkylamine, and the acid of the formula HX, wherein X is a halogen. The precursor solution may be stirred prior to, during, and/or after the addition of the metal halide, the capping ligand, the alkylamine, and the acid of the formula HX, wherein X is a halogen. The solvent may be a polar organic solvent. In one embodiment, the solvent is dimethylformamide (DMF).

The precipitating agent may be any agent capable of at least partially precipitating the metal halide perovskite nanoplatelets from the precursor solution. In one embodiment, the precipitating agent is a polar organic liquid. In a particular embodiment, the precipitating agent is acetone. The precipitating agent and the precursor solution generally may be contacted in any manner and in any order.

After the precursor solution and precipitating agent are contacted, a resulting supernatant may be removed by any means known in the art, such as filtration, decanting, centrifugation, etc. The metal halide perovskite nanoplatelets then may be dried by any means known in the art, such as air drying, drying under reduced pressure, vacuum oven, etc.

Composite Materials and Devices

Provided herein are composite materials that include a metal halide perovskite nanoplatelet and at least one other material. In embodiments, the composite materials comprise at least one metal halide perovskite nanoplatelet, and a matrix material. The at least one metal halide perovskite nanoplatelet may be disposed in the matrix material. In one embodiment, the metal halide perovskite nanoplatelet is substantially evenly dispersed in the matrix material.

The matrix material, in embodiments, is a host material. In one embodiment, the matrix material is a bipolar host material. The matrix material, in a particular embodiment, comprises poly(9-vinylcarbazole) (PVK). The matrix material, in a further embodiment, comprises 2-(4-biphenylyl)-5-phenyl-1,3,4-oxadiazole) (PBD). The matrix material, in a further embodiment, comprises a mixture of PVK and PBD. The PVK:PBD ratio may be about 70:30 to about 50:50. The PVK:PBD ratio, in a certain embodiment, is about 64:36.

Generally, the composite materials may be of any shape, and the metal halide perovskite nanoplatelets may be oriented in the composite materials in any manner. In one embodiment, the composite material is a film. In another embodiment, the composite material is a film, and a surface of the at least one metal halide perovskite nanoplatelet is substantially parallel to a surface of the film. In another embodiment, the composite material is a film, and the metal halide perovskite nanoplatelets are randomly oriented in the composite material.

The composite materials may be formed by any techniques known in the art. For example, the composite materials may be formed by spin casting or spin coating. The metal halide perovskite nanoplatelets, the matrix material, and a liquid may be combined and then spin casted or spin coated onto a surface.

Optoelectronic devices are provided herein, and the optoelectronic devices may include at least one metal halide perovskite nanoplatelet. The at least one metal halide perovskite nanoplatelet may be a light emitting material in the optoelectronic devices. In one embodiment, the optoelectronic devices include one or more of the composite materials provided herein.

In embodiments, the optoelectronic devices include a substrate, an electrode disposed on the substrate, and a counter electrode, wherein at least one metal halide perovskite nanoplatelet and/or a composite material as provided herein is arranged between the electrode and the counter electrode. The substrate may be a glass substrate. The electrode may include any suitable materials known in the art, such as indium tin oxide (ITO). The counter electrode may include any suitable materials known in the art, such as Al and LiF. The optoelectronic devices also may be sealed by any means known in the art. For example, the optoelectronic devices may be sealed with a resin, such as an epoxy resin.

The optoelectronic devices also may include a hole injection layer. The hole injection layer may be arranged between the electrode and the composite material and/or at least one metal halide perovskite nanoplatelet. The hole injection layer, in one embodiment, comprises PEDOT:PSS (poly(3,4-ethylenedioxythiophene):poly(styrenesulfonate).

The metal halide perovskite nanoplatelets provided herein may be arranged between the hole injection layer and a matrix material in the optoelectronic devices. In one embodiment, the metal halide perovskite nanoplatelets provided herein are in contact with and arranged between the hole injection layer and the matrix material. The matrix material may be selected from those of the composite materials provided herein, including PVK:PBD. Therefore, in embodiments, fabricating the optoelectronic devices herein comprises providing a hole transport layer, depositing the metal halide perovskite nanoplatelets on the hole transport layer, such as by spin coating, and then depositing the matrix material on the metal halide perovskite nanoplatelets, such as by spin coating.

The optoelectronic devices also may include an electron transport layer. The electron transport layer may be arranged between the counter electrode and the composite material or the one or more metal halide perovskite nanoplatelets. The electron transport layer may comprise BCP (bathocuproine, 50 nm). The electron transport layer also may function as a hole/exciton blocking layer.

The optoelectronic devices provided herein may be a photovoltaic cell, a light emitting diode, a light emitting electrochemical cell, a photodetector, or an optically pumped laser. The optoelectronic devices also may provide solid-state lighting, include full color displays, and/or emit white light.

In one embodiment, the optoelectronic device is a green PeLED (emission peak at 530 nm) that exhibits a maximum electroluminescence (EL) of 10590 cd m$^{-2}$ at 12 V. Not wishing to be bound by any particular theory, it is believed that the high luminescence of certain embodiments of the optoelectronic devices provided herein is due, at least in part, to the high luminescence of the metal halide perovskite nanoplatelets. Not wishing to be bound by any particular theory, it also is believed that the high luminescence of the metal halide perovskite nanoplatelets is facilitated, in some embodiments, by the optimized charge balance in the emitting layer, which may be provided by bipolar host materials, including PVK:PBD.

In embodiments, the optoelectronic devices provided herein can be assembled in an ambient environment. Not wishing to be bound by any particular theory, it is believed that the stability of the metal halide perovskite nanoplatelets in air with considerable humidity (~55%), at least in part, allows for the fabrication of the optoelectronic devices provided herein, including the PeLEDs, without an inert-gas glovebox. A glovebox-free procedure can simplify the synthesis and fabrication procedures, and, as a result, may be desirable and economic for scalable manufacturing.

One or more difficulties associated with optoelectronic device fabrication may be lessened by tailoring the capping ligands provided herein to facilitate the subsequent orthogonal deposition of charge transport layers in the optoelectronic devices, including the PeLED device. Therefore, it is believed that using the metal halide perovskite nanoplatelets provided herein as an emitter material can, in particular embodiments, simplify and ease optoelectronic device fabrication.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

In the Examples, the following materials were used, unless otherwise noted. PEDOT:PSS (Clevio P VP AI 4083) was purchased from Heraeus (Hanau, Germany). Methylamine solution ($CH_3NH_2$, 33% in absolute ethanol), lead bromide ($PbBr_2$), octylamine ($CH_3(CH_2)_7NH_2$, 99%), hydrobromic acid (48% in water), N,N-dimethylformamide (DMF, anhydrous, >99.8%), acetone ($CH_3COCH_3$, >99.9%), poly(9-vinylcarbazole) (PVK, average $M_n$ 25,000-50,000), 2-(4-biphenylyl)-5-phenyl-1,3,4-oxadiazole (PBD, 99%), bathocuproine (BCP, 99%), lithium fluoride (LiF, 99.995%), and aluminum (Al, evaporation slug, 99.999%) were purchased from Sigma-Aldrich (St. Louis, Mo., USA). Pre-patterned ITO-coated glass substrates (20 Ω/sq) were purchased from the Thin Film Devices Inc. (Anaheim, Calif., USA). All the chemicals except BCP were used without treatment. BCP was purified by sublimation before thermal evaporation.

Example 1

Synthesis of $MAPbBr_3$ Nanoplatelets

Colloidal nanoplatelets of methylammonium lead bromide ($MAPbBr_3$) perovskite were synthesized by adding 0.1 mmol $PbBr_2$, 0.16 mmol $CH_3(CH_2)_7NH_2$, 0.24 mmol methylamine (33% in absolute ethanol), and 0.5 mmol HBr sequentially into 200 µL DMF to form a mixture precursor solution.

After the solids were dissolved, the clear precursor solution was added into 3 mL acetone at room temperature, which produced a yellow-green colloidal solution.

The supernatant was discarded, and a yellow precipitate was collected and air dried after centrifugation at 4400 rpm for 10 min.

The $MAPbBr_3$ nanoplatelets were stable in ambient environment with humidity around 55% for at least one week, and were re-dispersed in toluene or acetone before device fabrication.

The as-prepared perovskite nanoparticles were substantially single crystalline nanoplatelets with varying size (50× 50 to 300×300 $nm^2$) and thickness (indicated by the contrast in the Transmission Electron Microscopy (TEM) images) (FIG. 1). Trace amount of spherical nanocrystals were found in the colloidal product.

Example 2

Fabrication of Devices

Using the metal halide perovskite nanoplatelets of Example 1 as a light emitting material, highly efficient LEDs exhibiting bright green EL centered at 530 nm with high color purity (FWHM 20 nm) were produced. A maximum luminance of 10590 cd $m^{-2}$ was achieved at a voltage of 12 V and a current density of 874 mA $cm^{-2}$ (FIG. 2), which was more than four times brighter than the current best-performing $MAPbBr_3$ nanoparticle-based LED (2000 cd $m^{-2}$) (Li G. et al. *Nano Lett.* 2015, 15, 2640).

ITO-coated glass substrates were sequentially cleaned by sonication in soap solution; rinsed with deionized water; sonicated in acetone and isopropyl alcohol for 15 min each; and dried with nitrogen gas flow. The substrates then were treated with UV ozone for 20 min prior to use.

A PEDOT:PSS solution was filtered by a 0.45 µm polytetrafluoroethylene (PTFE) syringe filter prior to use. The PEDOT:PSS solution was spin-coated onto the ITO substrates at 3000 rpm for 40 sec, following by heating at 140° C. for 20 min in air.

A solution containing $MAPbBr_3$ nanoplatelets (20 mg $mL^{-1}$ in acetone) and PVK:PBD (64/36 w/w, 4.65 and 2.0 mg $mL^{-1}$ in chloroform for PVK and PBD, respectively) was deposited layer by layer by spin coating at 6000 rpm for 30 sec. The PVK:PBD layer was baked at 60° C. for 1 min. The steps were finished in air with a humidity of about 55%.

Finally, BCP (50 nm), LiF (1 nm) and Al (150 nm) were deposited using thermal evaporation through shadow masks at a rate of 2.0 Å $s^{-1}$, 0.2 Å $s^{-1}$, and 4 Å $s^{-1}$, respectively, under a high vacuum (<$3\times10^{-6}$ Torr).

The LEDs were formed at the 2×2 mm squares where the ITO (anode) and Al (cathode) stripes intersected. The device was sealed with a piece of glass coverslip and epoxy resin to reduce the decay of the moisture-sensitive BCP layer within 1 hour of fabrication. High brightness was achieved by using a multilayer device architecture.

To demonstrate reproducibility, 13 devices which exhibited on average the peak luminance 8057 cd $m^{-2}$ were randomly selected and tested, as explained herein at Example 3.

Not wishing to be bound by any particular theory, it was believed that the PEDOT:PSS (20 nm) acted as a hole-injection layer, the PVK:PBD (64/36 weight ratio, 30 nm) as the bipolar host, and the BCP (bathocuproine, 50 nm) as the electron transport and hole/exciton blocking layer. It was believed that the bright green electroluminescence primarily arose from the use of the highly emissive perovskite nanoplatelets of Example 1.

Figure 3:
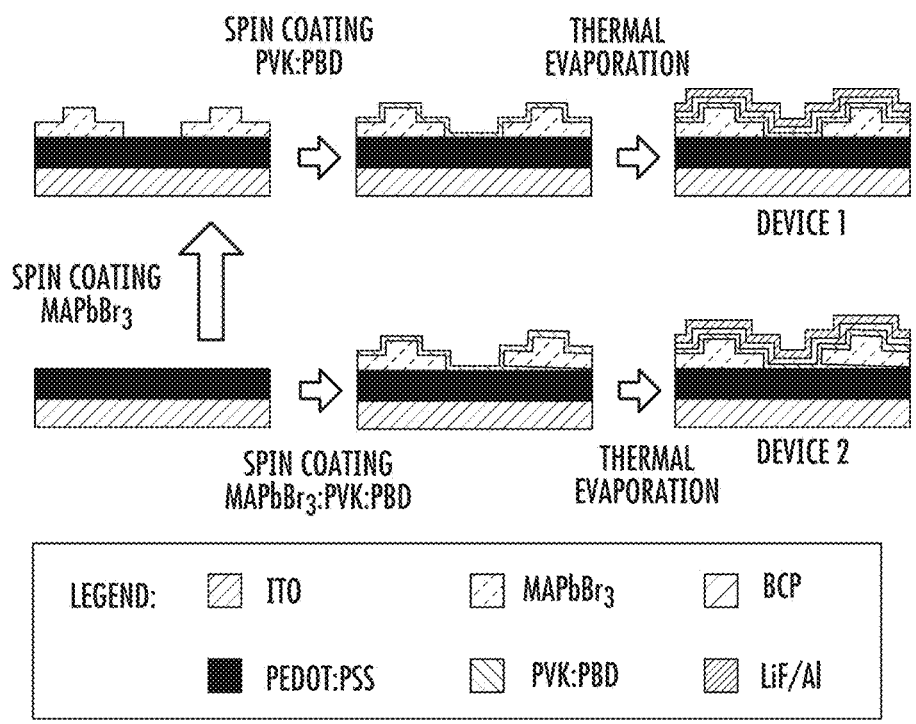
FIG. 3 is a schematic of two embodiments of a device fabrication process, and two embodiments of an optoelectronic device.

The emitter/bipolar host structure demonstrated also was achieved by an alternative one-step spin coating process. The perovskite nanoplatelets of Example 1 (15 mg) were dispersed in a chloroform solution (1 mL) containing PVK and PBD (9.33 mg and 6.22 mg for PVK and PBD, respectively) to form a colloidal precursor solution. Then the $MAPbBr_3$:PVK:PBD precursor solution was spin-coated onto the PEDOT:PSS film at 1,500 rpm for 40 sec. BCP (50 nm), LiF (1 nm), and Al (150 nm) were successively deposited by vacuum thermal evaporation. The PeLED device made by this process was denoted as Device 2 (see FIG. 3). As a comparison, the PeLED device with the separated spin coating processing of perovskite and PVK: PBD layer was denoted as Device 1 (see FIG. 3). It was observed that using a pre-mixed $MAPbBr_3$ and PVK:PBD blend precursor solution for emitting layer deposition resulted in a higher EQE (0.54%) in several of the PeLED devices of this example, although the brightness was lessened, likely because of less efficient charge injection.

AFM characterizations of the emissive $MAPbBr_3$: PVK: PBD layer in Device 2 revealed that the perovskite coverage and the blend film surface roughness were similar to that of Device 1. However, not wishing to be bound by any particular theory, it was believed that the usage of pre-mixed $MAPbBr_3$:PVK:PBD precursor solution might have resulted in a better perovskite nanoplatelet distribution in the bipolar PVK:PBD polymeric host, which may have cause a more favorable recombination zone near the center of the emissive layer, and prevented exciton quenching. Device 2 showed a clear increase in quantum efficiency. Particularly, the EQE was more than doubled—from 0.26% in Device 1 to 0.54% in Device 2.

Figure 4:
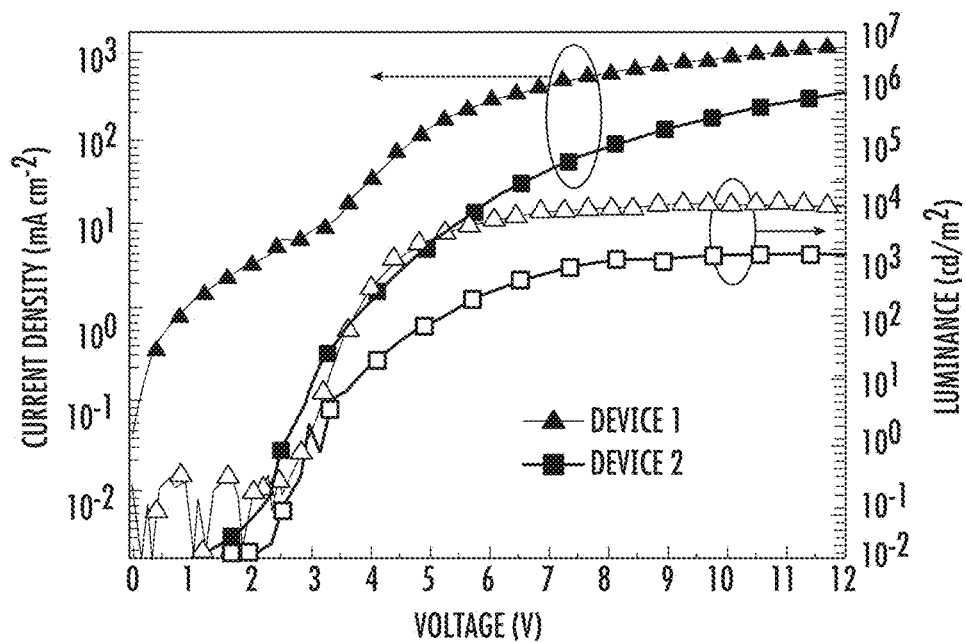
FIG. 4 is a plot of current density and luminance versus voltage for the optoelectronic devices of FIG. 3.

Also, due to the reduced spin-coating rate, the thickness of the PVK:PBD blend layer in Device 2 (~73 nm) was thicker than that of Device 1 (~30 nm). It was believed that this difference caused Device 2 to exhibit a much lower current density at each driving voltage than Device 1, which lead to a limited luminance (FIG. 4). The maximum luminance of Device 2 was 1,548 cd m$^{-2}$, which was one-sixth times smaller than that of Device 1.

Figure 2:
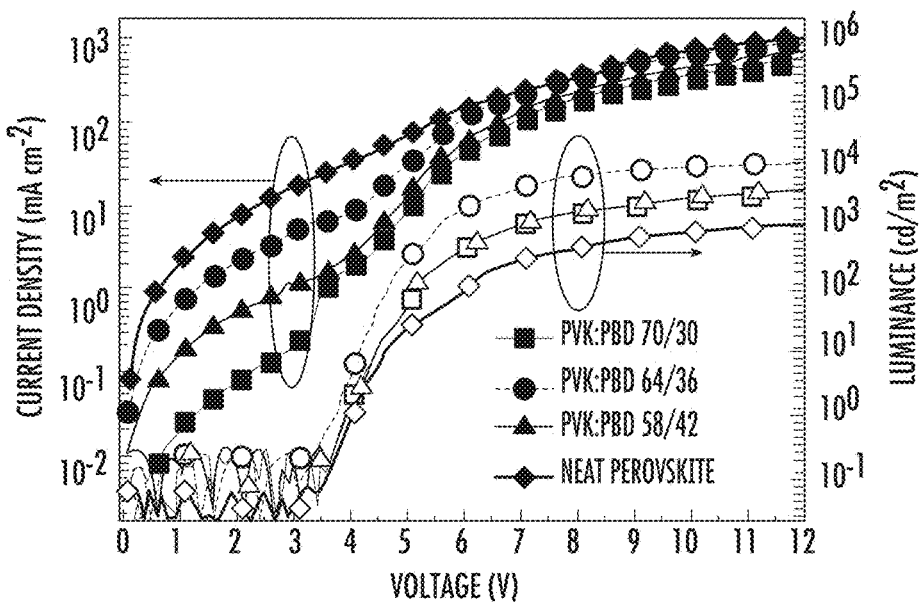
FIG. 2 is a plot of current density and luminance versus voltage for several embodiments of optoelectronic devices.
Figure 5:
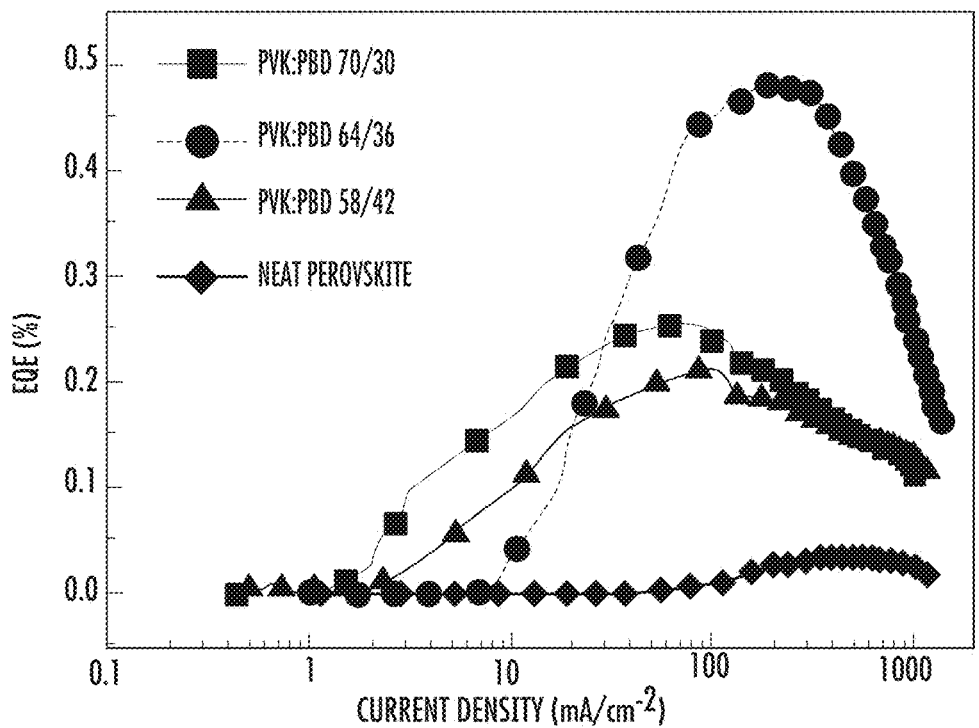
FIG. 5 is a plot of the external quantum efficiency (EQE) versus current density for several embodiments of optoelectronic devices.

Not wishing to be bound by any particular theory, the addition of the PVK:PBD layer was believed to improve the charge transport properties. A control device without the PVK:PBD layer was fabricated and compared with standard devices. The control device produced a maximum luminance of 1113 cd m$^{-2}$ when driven at 12V (FIG. 2). However, low peak EQE of 0.038% and power efficiency of 0.04 lm W$^{-1}$ were observed, which was believed to be due to the high current leak via the pinholes of the perovskite nanoplatelet emitting layer. All of the standard PeLED devices of this example with the PVK:PBD layer exhibited reduced current density and enhanced brightness, and lead to higher EQE than that of the control device (FIG. 2 and FIG. 5). Not wishing to be bound by any particular theory, this was believed to indicate that the addition of the bipolar PVK:PBD polymer removed the pinholes in the perovskite emitting layer, and/or suppressed the non-radiative current losses.

Furthermore, the tunable electron and hole transport properties was optimized by adjusting the weight ratios of the PVK:PBD blend to obtain optimal charge transport and balance between electrons and holes. It was believed that this tuning permitted optimal performance of the LEDs to be achieved by keeping the recombination zone near the center of the emissive layer and preventing exciton quenching. By increasing the PBD weight ratio, from 70:30 (PVK:PBD) to 64:36, an increased overall current density and a reduced turn-on voltage (the voltage with a luminance 1 cd m$^{-2}$) was observed (Table 1).

TABLE 1

Device Characteristics of PeLEDs with or without PVK:PBD Layer

| PVK:PBD w/w ratio | Turn-on voltages [V] | Max Luminance [cd m$^{-2}$] | Max EQE [%] | Max Power Efficiency [lm W$^{-1}$] |
|---|---|---|---|---|
| 70/30 | 3.9 | 3640 | 0.26 | 0.55 |
| 64/36 | 3.8 | 10590 | 0.48 | 1.0 |
| 58/42 | 4.1 | 4114 | 0.21 | 0.44 |
| N/A | 4.1 | 1113 | 0.038 | 0.04 |

This phenomenon was believed to suggest that in the PeLEDs of this example, the performance was dictated, at least in part, by electron injection. An optimal charge injection was achieved with a PVK:PBD ratio 64:36 which led to the highest luminance of 10590 cd m$^{-2}$ at a voltage of 12 V (FIG. 2 and FIG. 5). The peak external quantum efficiency (EQE) of 0.48% was reached at 6.6 V with the luminance of 3494 cd m$^{-2}$, which was believed to suggest that the device's performance was comparable to the previously reported high-performance green PeLEDs (Table 2). Further increasing the PBD weight to a PVK:PBD ratio of 58:42 reduced the device maximum brightness to 4114 cd m$^{-2}$ and to 0.21%, and these changes were believed to be caused an imbalanced electron-hole injection rate. The average luminance and EQE value for devices collected from different batches exhibited the same trend of device performance with the tuning of PVK:PBD ratio.

TABLE 2

Comparison of our device with other reported green PeLEDs

| Device configuration | Turn-on voltages [V] | Max EQE [%] | Max Luminance [cd m$^{-2}$] | Voltage for Max Luminance [V] | Reference |
|---|---|---|---|---|---|
| ITO/PEDOT:PSS/CH$_3$NH$_3$PbBr$_3$/F8/Ca/Ag | 3.3 | 0.1 | 364 | 6.5 | Z.-K. Tan et al. *Nat Nano* 2014, 9, 687. |
| PET/ITO/Buf-HIL*/CH$_3$NH$_3$PbBr$_3$/TPBI/LiF/Al | 3.2 | 0.125 | 417 | 7.6 | Y.-H. Kim et al. *Advanced Materials* 2015, 27, 1248. |
| ITO/PEDOT:PSS/CH$_3$NH$_3$PbBr$_3$/TmPyPB/LiF/Al | 3.5 | 0.1 | 1500 | 8 | X. Qin et al. *Science China Materials* 2015, 58, 186. |
| ITO/PEDOT:PSS/Perovskite-PIP/F8/Ca/Ag | 3.2 | 1.2 | 1,000‡ | 4.5 | G. Li et al. *Nano Letters* 2015, 15, 2640. |
| ITO/c-TiO$_2$/EA/CH$_3$NH$_3$PbBr$_3$/SPB-02T/MoO$_3$/Au | 2.9 | 0.051 | 544.65 | 5.8 | J. C. Yu et al. *Advanced Materials* 2015, 27, 3492. |
| ITO/ZnO/PEI/MAPbBr$_3$/TFB/MoO$_x$/Au | 2.1 | 0.8 | 20,000 | 2.8 | J. Wang et al. *Advanced Materials* 2015, 27, 2311. |

TABLE 2-continued

Comparison of our device with other reported green PeLEDs

| Device configuration | Turn-on voltages [V] | Max EQE [%] | Max Luminance [cd m$^{-2}$] | Voltage for Max Luminance [V] | Reference |
|---|---|---|---|---|---|
| ITO/MAPbBr$_3$-PEO/In/Ga | 2.9 | 0.083 | 2,500 | 4.5 | J. Li et al. Advanced Materials 2015, 27, 5196. |
| ITO/PEDOT:PSS/MAPbBr$_3$/PBK:PBD/BCP/ LiF/Al | 3.8 | 0.48 | 10,590 | 12 | Inventive PeLED |

| Device configuration | EQE [%] | Luminance [cd m$^{-2}$] @ voltage [V] | Reference |
|---|---|---|---|
| ITO/PEDOT:PSS/MAPbBr$_3$/PBK:PBD/BCP/ LiF/Al | 0.48 | 3,500 @ 6.6 | Inventive PeLED |
|  | 0.46 | 6,590 @ 8.0 | Inventive PeLED |

*Buf-HIL is a self-organized buffer hole-injection layer (Buf-HIL) composed of PEDOT:PSS and a perfluorinated polymeric acid, tetrafluoroethylene-perfluoro-3,6-dioxa-4-methyl-7-octene-sulfonic acid copolymer (PFI).
‡The maximum luminance (1,000 cd m$^{-2}$) was chosen from the device with 1:2 PIP to perovskite ratio due to its peak EQE of ~1%, instead of the device with 1:10 PIP to perovskite ratio which exhibited the highest luminance (~2,000 cd m$^{-2}$) with a low EQE of 0.25%.

The bipolar PVK:PBD host was believed to be important in this example for optimizing the film morphology, the charge transport, and the recombination. The blend of the hole-transport PVK matrix and the electron-transport PBD has been widely used as the host material for guest emitters in organic LEDs.

Spin casting a chloroform solution of PVK:PBD blends on top of the pre-deposited perovskite-nanoplatelets film allowed for the construction of multilayered structures, due to the low solubility of perovskite-nanoplatelets in chloroform. The addition of the PVK:PBD blend layer was believed to improve the interfacial quality by removing the pinholes and/or reducing the roughness of the perovskite nanoplatelet emitting layer. AFM images revealed that the neat perovskite nanoplatelet layer had a rough film morphology with aggregated perovskite stacks and pinholes, which were believed to be caused by the low geometric curvature of nanoplatelets, which, in turn, was believed to be caused by the strong interaction among the capping ligands. The surface roughness was reduced from 45.3 nm to 34.6 nm after the metal halide perovskite nanoplatelets were capped with PVK:PBD, according to cross-section profiles of MAPbBr$_3$ stacks on top of the PEDOT:PSS layer before and after being capped with a PVK:PBD layer. It was observed that the coverage of perovskite nanoplatelets did not change with the addition of the bipolar polymeric capping layer, which was believed to be due to the low solubility of perovskite nanoplatelets in the chloroform solvent of the PVK:PBD precursor solution.

Not wishing to be bound by any particular theory, it was believed that the insulating nature of the organic semiconductors and possibly the capping ligand on the surface of the perovskite nanoplatelet emitter together increased the overall resistivity of certain PeLEDs of this example. Unlike other PeLEDs with fewer or no organic layers, a higher bias (~12 V) was needed to achieve high charge density for efficient radiative recombination in several devices of this example.

Example 3

Characterization of MAPbBr$_3$ Nanoplatelets and Devices

Transmission Electron Microscopy: Transmission electron microscopy images were obtained with a JEM-ARM200cF (JEOL USA, Inc., Mass., USA) operated at 200 kV. For conventional TEM studies, the colloidal MAPbBr$_3$ nanoplatelet precursor of Example 1 (20 mg mL$^{-1}$ in acetone) was spin-coated onto Cu/lacey-carbon TEM grids.

Atomic Force Microscopy: Atomic force microscopy images were taken with an Icon scanning probe microscope (Bruker, USA) in tapping-mode.

X-ray Diffraction: The MAPbBr$_3$ nanoplatelet on a glass substrate was characterized by a X'PERT Pro powder X-ray diffractometer (PANalytical, USA). Diffraction patterns were recorded from 10 to 50° 2θ with a step size of 0.02° at 1° min$^{-1}$.

Figure 6:
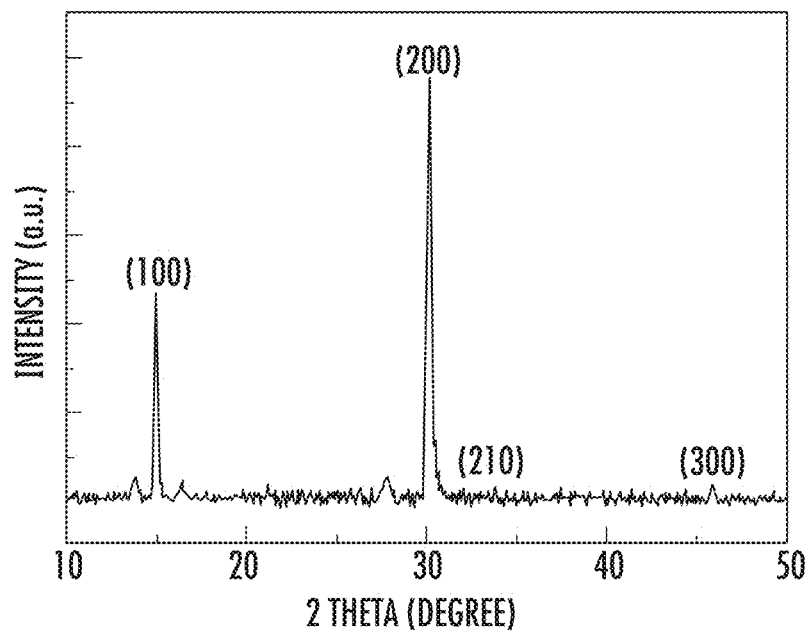
FIG. 6 depicts an X-ray diffraction pattern of one embodiment of a film including metal halide perovskite nanoplatelets.

The X-ray diffraction (XRD) pattern showed that the nanoplatelets of Example 1 had a cubic lattice structure with a unit cell of 5.93 Å, which was close to that of bulk MAPbBr$_3$ perovskites (FIG. 6). Two satellite peaks by the side of the intense (100) peak likely originated from the unoriented layered organometal halide perovskites. The selected area electron diffraction (SAED) pattern was believed to suggest that the free-standing perovskite nanoplatelets of Example 1 were single crystalline, and had the same (001) facets exposed (FIG. 1, inset), which was consistent with the XRD results.

Luminescence: The photoluminescence and electroluminescence spectra were measured on a iHR320 spectrofluorimeter (HORIBA Scientific, USA), equipped with a HORIBA Synapse CCD detection system. A 100 W 20V mercury short arc lamp coupled with a 420 nm long pass filter was used as the excitation light source.

The XRD and PL intensity were used to show the stability of the solid-state (dried) MAPbBr$_3$ perovksite nanoplatelets of Example 1. Both XRD patterns and PL intensity remained stable over a course of 7 days when exposed to the ambient environment with a humidity of 50-60%. Both the crystal structure and the optical properties of MAPbBr$_3$ nanoplatelets of Example 1 were well retained. It was believed that the improved moisture resistance of the nanoplatelets could be explained by the hydrophobic long-chain capping ligand, which likely shielded the inner hygroscopic MAPbBr$_3$ perovskite layers of Example 1 from moisture, thus attenuating the process of water-induced degradation. The moisture-resistance was believed to reduce the requirements on the infrastructure for device fabrication, and may also lead to better device performance.

To study the stability, X-ray diffraction patterns and PL intensities were collected of the solid state MAPbBr$_3$ nanoplatelets of Example 1 distributed on a piece of clean glass substrate by spin coating during the one-week period. This solid film was stored in ambient air with a humidity of ~50-60% during the interval of each measurement. The XRD pattern illustrated that after exposure to such a high humidity for 7 days, the crystal structure of MAPbBr$_3$ nanoplatelet was retained. Additionally, the PL intensities were also stable with a small fluctuation during the one-week test. Hence, the above XRD and PL intensity data, as well as the overlapped PL decay curves, confirmed that the MAPbBr$_3$ perovskite nanoplatelets of Example 1 could maintain both their crystal structure and optical properties after exposure to air with ~60% humidity.

Electrical and Optical Intensity: The electrical and optical intensity characteristics of the devices were measured with a Keithly 4200 sourcemeter/multimeter (Tektronix, USA) coupled to a Thorlabs FDS 1010 Si photodiode. Only light emitting from the front face of the device was collected and used in subsequent efficiency calculations. The emission was found to be uniform throughout the area of each device.

Emission Data: Steady-state and time-resolved emission data were collected at room temperature using an Edinburgh FLS980 spectrometer (Edinburgh Instruments, USA).

Samples were excited using light output from a housed 450 W Xe lamp passed through a single grating (1800 l/mm, 250 nm blaze) Czerny-Turner monochromator and finally a 5 nm bandwidth slit. Emission from the sample was first passed through a 495 nm long-pass color filter, then a single grating (1800 l/mm, 500 nm blaze) Czerny-Turner monochromator (5 nm bandwidth) and finally detected by a Peltier-cooled Hamamatsu R928 photomultiplier tube.

The dynamics of emission decay were monitored by using the FLS980's time-correlated single-photon counting capability (1024 channels; 5 ms window) with data collection for 10000 counts. Excitation was provided by an Edinburgh EPL-405 picosecond pulsed diode laser (400.4 nm, 57.6 ps FWHM) operated at 200 kHz.

PL quantum yield measurements: The perovskite nanoplatelets of Example 1 exhibited bright photoluminescence (PL) at 529 nm with a narrow spectral band (full width at half maximum, FWHM, ~20 nm) and a quantum yield up to 85%.

Emission quantum yields were acquired using an integrating sphere incorporated into a spectrofluorometer (FLS980, Edinburgh Instruments). Quantum yield was then calculated by using the Edinburg L980 software package.

PL quantum yield (PL QY) for both MAPbBr$_3$ nanoplatelets of Example 1 in toluene solution and in solid-state thin film were measured at room temperature using an Edinburgh FLS980 spectrometer. The solid-state thin films were prepared by drop-drying the same MAPbBr$_3$ nanoplatelets (of Example 1) toluene solution on pre-washed glass substrates. Samples were excited by 405 nm light from a housed 450 W Xe lamp combined with a single grating (1800 l/mm, 250 nm blaze) Czerny-Turner monochromator and finally a 5 nm bandwidth slit. Emission quantum yields were acquired using an integrating sphere incorporated into a spectrofluorometer (FLS980, Edinburgh Instruments). Quantum yield was then calculated by using the Edinburg L980 software package.

Figure 7:
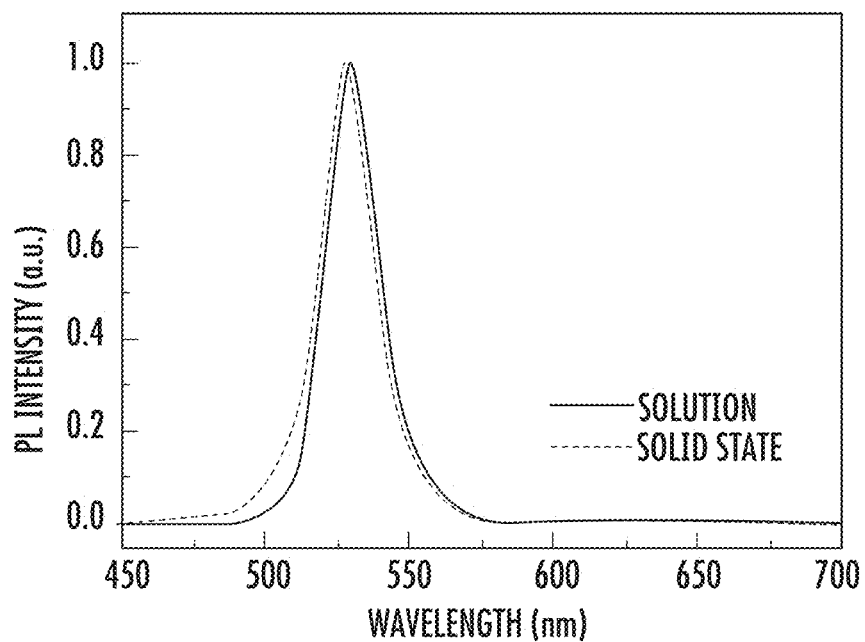
FIG. 7 is a plot of photoluminescent (PL) intensity versus wavelength for an embodiment of metal halide perovskite nanoplatelets in a solid state and in toluene.

The PL QY of the MAPbBr$_3$ nanoplatelets of Example 1 were ~65-85% and ~18-21% for the samples in toluene solution and solid-state thin films, respectively. Specifically, strong PL was observed from the MAPbBr$_3$ nanoplatelets of Example 1 under UV irradiation (Hg lamp, 365 nm), either dispersed in toluene or dried as solid films (FIG. 7). The PL spectrum showed a well-defined peak at 529 nm with low FWHM of 20 nm (FIG. 7). Using a fluorescence spectrometer with an integrated sphere, it was discovered that the PL quantum yield of the MAPbBr$_3$ nanoplatelets of Example 1 in toluene solution could be as high as ~65-85%, which was one order of magnitude higher than what was typically reported from bulk polycrystalline MAPbBr$_3$ perovskites.

The reduced PL QY of the thin films was believed to be due to the self-absorption, which was expected for direct bandgap luminescent materials. Nevertheless, both the PL QY in solution and in solid states were higher than what was typically reported for bulk polycrystalline MAPbBr$_3$ perovskites (~7%) (Friend, R. H. et al. *Nature* 1999, 397, 121), which indicated a lower non-radiative recombination rate, which may have been due to the surface passivation by the capping ligand and/or the reduced defect density in the small single crystalline nanoplatelets.

Time-resolved PL decay results and discussion: Also measured was the time-resolved PL spectrum of the diluted MAPbBr$_3$ perovskites (of Example 1) toluene solution to determine the exciton recombination lifetime. The triexponential fitting of the PL decay gave the average recombination lifetime ($\tau_{ave}$) of ~2.7 µs, which was longer than that of a bulk MAPbBr$_3$ film (~100 ns)(Zhang, M. et al. *Chem. Commun.* 2014, 50, 11727). Such prolonged radiative lifetime and high quantum yield together were believed to indicate an extraordinarily low non-radiative recombination rate in the perovskite nanoplatelets of Example 1, which was believed to be due to the surface passivation by the octylammonium bromide capping ligand, and/or the reduced defect density in the nanoscale single crystals. Besides surface passivation, the long-chain capping ligands also were believed to make the MAPbBr$_3$ nanoplatelets highly resistant to moisture.

The recombination lifetime of the MAPbBr$_3$ nanoplatelets of Example 1 was determined by measuring PL decay at the emission peak wavelength (529 nm). The time-resolved PL decay curves were fitted with a triexponential function of time (t):

$$R(t) = B_1 e^{\left(-\frac{t}{\tau_1}\right)} + B_2 e^{\left(-\frac{t}{\tau_2}\right)} + B_3 e^{\left(-\frac{t}{\tau_3}\right)}$$

where $B_i$ (i=1,2,3) are prefactors and $\tau_i$ (i=1, 2, 3) were the time constants. The average recombination lifetime ($\tau_{ave}$) was estimated with the $B_i$ and $\tau_i$ value from the fitted curve data according to the following equation:

$$\tau_{ave} = \Sigma B_i \tau_i^2 / B_i \tau_i, i=1,2,3$$

The fitting results are listed in the following table:

| | $\tau_1/\mu s$ | $B_1$ | $\tau_2/\mu s$ | $B_2$ | $\tau_3/\mu s$ | $B_3$ | $\tau_{ave}/\mu s$ |
|---|---|---|---|---|---|---|---|
| fresh sample | 0.20591 | 2277.3 | 1.1997 | 977.76 | 6.2176 | 145.78 | 2.7006 |
| 1 month sample | 0.20623 | 2305.4 | 1.0063 | 870.49 | 6.1568 | 150.92 | 2.9374 |

Compared to bulk MAPbBr$_3$ film (PL $\tau_{ave}$ of ~100 ns), the average recombination lifetime of the nanoplatelets of Example 1 ($\tau_{ave}$ of ~2.7 µs) was much longer. It was observed that the MAPbBr$_3$ nanoplatelets of Example 1 exhibited high PL quantum yields of ~65-85%. The trend that highly emissive perovskite materials have prolonged PL lifetime has been observed in mixed halide perovskite MAPbBr$_{3-x}$Cl$_x$ (x=0-1.2) with different compositions of halogens, which indicated an extraordinary low non-radiative recombination rate in the perovskite nanoplatelet of Example 1, likely due, at least in part, to the surface passivation by the capping ligand and/or the reduced defect density in nanoscale single-crystalline. Additionally, considering that the MAPbBr$_3$ perovskite nanoplatelets of Example 1 exhibited obvious self-absorption in PL spectra, it was believed that photon recycling also may have played an important role in the excited state dynamics, which has been observed in surface-passivated GaAs films with a long radiative lifetime.

PL lifetime measurements also were carried out for a fresh-prepared sample and an old sample stored in ambient air with a humidity of 50-60% for at least one month. Both solid samples were dispersed in neat toluene using mild sonication and stirring just before the time-dependent PL measurement. The well overlapping of these two PL spectra, as well as the similar $\tau_{ave}$ from fitting result, confirmed that the MAPbBr$_3$ perovskite nanoplatelets of Example 1 exhibited excellent stability when exposed ~60% humidity.

Average Performance and Reproducibility of PeLEDs: Multiple measurements were collected for devices with and without PVK:PBD from three batches. The mean value, median, and standard deviation were calculated based on 40 devices. The device numbers were 12, 13, 10 and 5 for PVK:PBD 70/30, 64/36, 58/42, and not PVK:PBD, respectively. The average maximum luminance of ~8000 for devices with a PVK:PBD ratio 64:36 indicated an encouraging reproducibility of the optimum condition.

We claim:
1. A metal halide perovskite comprising:
a nanoplatelet comprising an alkylammonium metal halide and a capping ligand;
wherein the nanoplatelet has a surface having a width of about 100 nm to about 300 nm and a length of about 100 nm to about 300 nm, and
the capping ligand comprises a compound of formula (1),

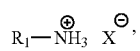

(1)

wherein R$_1$ is a monovalent C$_1$-C$_{20}$ hydrocarbyl, and X is Cl or I.
2. The metal halide perovskite of claim 1, wherein R$_1$ is a monovalent C$_6$-C$_{20}$ hydrocarbyl.
3. The metal halide perovskite of claim 1, wherein the alkylammonium metal halide is an alkylammonium lead halide, alkylammonium tin halide, alkylammonium germanium halide, alkylammonium manganese halide, alkylammonium cobalt halide, alkylammonium bismuth halide, or alkylammonium europium halide.
4. The metal halide perovskite of claim 1, wherein the alkylammonium metal halide is a methylammonium lead halide.
5. The metal halide perovskite of claim 1, wherein the nanoplatelet is a single crystalline nanoplatelet.
6. A composite material comprising:
at least one nanoplatelet comprising an alkylammonium metal halide and a capping ligand; and
a solid matrix material; wherein the at least one nanoplatelet is disposed in the matrix material, the at least one nanoplatelet has a surface having a width of about 50 nm to about 300 nm and a length of about 50 nm to about 300 nm, and the capping ligand comprises a compound of formula (1),

(1)

wherein R$_1$ is a monovalent C$_1$-C$_{20}$ hydrocarbyl, and X is Cl, Br, or I.
7. The composite material of claim 6, wherein the capping ligand is n-octylammonium bromide:

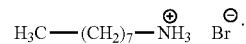

8. The composite material of claim 6, wherein the alkylammonium metal halide is a methylammonium lead bromide.
9. The composite material of claim 6, wherein the alkylammonium metal halide is methylammonium lead bromide, and the capping ligand is n-octylammonium bromide.
10. The composite material of claim 6, wherein the matrix material comprises PVK and PBD at a PVK:PBD weight ratio of about 70:30 to about 50:50.
11. The composite material of claim 6, wherein the composite material is a film, and a surface of the at least one nanoplatelet is substantially parallel to a surface of the film.
12. An optoelectronic device comprising:
at least one metal halide perovskite, wherein the at least one metal halide perovskite (i) is a light emitting material, and (ii) comprises a nanoplatelet comprising an alkylammonium metal halide and a capping ligand, wherein the nanoplatelet has a surface having a width of about 100 nm to about 300 nm and a length of about 100 nm to about 300 nm, and the capping ligand comprises a compound of formula (1),

(1)

wherein $R_1$ is a monovalent $C_1$-$C_{20}$ hydrocarbyl, and X is Cl, Br, or I.

13. The optoelectronic device of claim 12, further comprising a matrix material, wherein the at least one metal halide perovskite is disposed in the matrix material.

14. The optoelectronic device of claim 13, wherein the matrix material is a bipolar host matrix material comprising PVK and PBD at a PVK:PBD weight ratio of about 70:30 to about 50:50.

15. The optoelectronic device of claim 12, further comprising:
    a substrate,
    an electrode disposed on the substrate, and
    a counter electrode, wherein the at least one metal halide perovskite is arranged between the electrode and the counter electrode.

16. The optoelectronic device of claim 15, further comprising a hole injection layer arranged between the electrode and the at least one metal halide perovskite.

17. The optoelectronic device of claim 16, wherein the hole injection layer comprises PEDOT:PSS.

18. The optoelectronic device of claim 16, wherein the at least one metal halide perovskite is in contact with and arranged between the hole injection layer and a matrix material.

19. The optoelectronic device of claim 18, wherein the matrix material comprises PVK and PBD at a PVK:PBD weight ratio of about 70:30 to about 50:50.

20. The optoelectronic device of claim 15, further comprising an electron transport layer, wherein the electron transport layer is arranged between the counter electrode and the at least one metal halide perovskite.

21. The optoelectronic device of claim 20, wherein the electron transport layer comprises BCP.

22. The optoelectronic device of claim 12, wherein the optoelectronic device is a photovoltaic cell, a light emitting diode, a light emitting electrochemical cell, a photodetector, or an optically pumped laser.

* * * * *